United States Patent [19]

Birkmann et al.

[11] Patent Number: 4,963,482

[45] Date of Patent: Oct. 16, 1990

[54] DNA FOR THE REPRESSIBLE AND INDUCIBLE EXPRESSION OF FOREIGN GENES

[75] Inventors: Angelika Birkmann, Munich; August Böck, Geltendorf, both of Fed. Rep. of Germany

[73] Assignee: Boehringer Mannheim GmbH, Mannheim, Fed. Rep. of Germany

[21] Appl. No.: 175,780

[22] Filed: Mar. 31, 1988

[30] Foreign Application Priority Data

Mar. 31, 1987 [DE] Fed. Rep. of Germany ....... 3710633
Oct. 19, 1987 [DE] Fed. Rep. of Germany ....... 3735381

[51] Int. Cl.$^5$ .................... C12P 21/00; C12N 15/00; C07H 21/04
[52] U.S. Cl. .................... 435/69.1; 435/71.2; 435/172.3; 435/320; 536/27; 935/6; 935/8; 935/39
[58] Field of Search ............... 435/68, 172.1, 172.3, 435/91, 320, 252.3, 252.31–252.35, 6, 69.1, 71.2; 536/27; 935/6, 8, 39, 72–75

[56] References Cited

PUBLICATIONS

Birkmann et al., Arch Microbiol 148:44–51, (1987).
Hirschman et al; Proc. Natl. Acad. Sci. USA, 82:7525, (1985).
Birkmann et al., Mol. Gen. Genet 210:535–542, (1987).
Reitzer et al., Cell 45:785–792.
Buck et al., Nucl. Acids Res, 13(21): 7621–7636, (1985).
Gussin et al., Ann. Rev. Genet 20:567–591, (1986).

*Primary Examiner*—James Martinell
*Attorney, Agent, or Firm*—Felfe & Lynch

[57] ABSTRACT

The present invention provides a recombinant DNA, wherein it contains the consensus sequence:

```
   T    TTTC   T         A  A    T
AT   TCG      G  CACGTC  A  AC   G
G        AAAT A         G  C    G
``` and a promoter which has the DNA sequence $GGN_{10}GC$.

The present invention also provides a process for the isolation of this recombinant DNA, wherein a DNA sequence containing the consensus sequence is identified from a gene bank of a micro-organism, which contains a gene which is repressible by oxygen and inducible by formate under anaerobic conditions, isolated and combined with an appropriate promotor according to known methods.

This recombinant gene can be used for the inducible and repressible expression of a foreign gene by bringing about the induction by formate under anaerobic conditions and the repression by oxygen.

25 Claims, 3 Drawing Sheets

FIG. 1

Sequence of fdhF

```
          10        20        30        40        50        60        70        80
(SmaI)
GGGCGCTGCCGGCACCTGTCCTACGAGTTGCATGATAAAGAAGACAGTCATAAGTGCGGCGACGATAGTCATGCCCCGCG 90       100       110       120       130       140       150       160
CCCACCGGAAGGAGCTACCGGCAGCGGTGCGGACTGTTGTAACTCAGAATAAGAAATGAGGCCGCTCATGGCGTTGGTCT 170       180       190       200       210       220       230       240
GAAATTGCCGCTGTTTGACGGTGGACGGTTGAATGCCAATCTCGAAGGCACGCGCGCCGCCAGCAACATGATGATTGAAC 250       260       270       280       290       300       310       320
GTTACAACCAGTCAGTACTGAACGCGGTGCGTGACGTTGCCGTCAACGGCACGCGTCTGCAAACGCTCAACGACGAGCGA 330       340       350       360       370       380       390       400
GAAATGCAGGCTGAACGCGTGGAAGCCACGCGCTTTACCCAGCGCGCTGCCGAGGCCGCCTATCAGCGCGGCTTAACCAG 410       420       430       440       450       460       470       480
CCGCTTACAGGCCACCGAAGCCCGGTTGCCAGTGCTTGCCGAAGAGATGTCATTACTGATGCTGGACAGCCGCCGGGTGA
                                       ┌──── pBN208
         490       500       510       520       530       540       550       560
TCCAAAGCATTCAGTTGATGAAATCGCTGGGCGGCGGGTATCAGGCAGGTCCCGTCGTCGAGAAAAAATAAAATGTCTGC
    ┌──── pBN210                           ┌──── pBN211
         570       580       590       600       610       620       630       640
CGCGTGATGGCTGTCACGCGGTATTTCGTTTCGTCACGTCAAAACTGACGACAGCCTGTTTTTCGTCAGAGTTTTGAATA
                                                                     ┌── mRNA
         650       660       670       680       690       700       710       720
AATAGTGCCCGTAATATCAGGGAATGACCCCACATAAAATGTGGCATAAAAGATGCATACTGTAGTCGAGAGCGCGTATG 730       740       750       760       770       780       790       800
CGTGATTTGATTAACTGGAGCGAGACCGATGAAAAAAGTCGTCACGGTTTGCCCCTATTGCGCATCAGGTTGCAAAATCA
                   SD           
         810       820       830       840       850       860    KpnI 870       880
ACCTGGTCGTCGATAACGGCAAAATCGTCCGGGCGGAGGCAGCGCAGGGGAAAACCAACCAGGGTACCCTGTGTCTGAAG
                                                                        pBN2
         890       900       910       920       930       940       950       960
GGTTATTATGGCTGGGACTTCATTAACGATACCCAGATCCTGACCCCGCGCCTGAAAACCCCCATGATCCGTCGCCAGCG 970       980       990      1000      1010      1020      1030      1040
TGGCGGCAAACTCGAACCTGTTTCCTGGGATGAGGCACTGAATTACGTTGCCGAGCGCCTGAGCGCCATCAAAGAGAAGT 1050      1060      1070      1080      1090      1100      1110      1120
ACGGTCCGGATGCCATCCAGACGACCGGCTCCTCGCGTGGTACGGGTAACGAAACCAACTATGTAATGCAAAAATTTGCG 1130      1140      1150      1160      1170      1180      1190      1200
CGCGCCGTTATTGGTACCAATAACGTTGACTGCTGCGCTCGTGTCTGACACGGCCCATCGGTTGCAGGTCTGCACCAATC 1210      1220      1230      1240      1250      1260      1270      1280
GGTCGGTAATGGCGCAATGAGCAATGCTATTAACGAAATTGATAATACCGATTTAGTGTTCGTTTTCGGGTACAACCCGG 1290      1300      1310      1320      1330      1340      1350      1360
CGGATTCCCACCCAATCGTGGCGAATCACGTAATTAACGCTAAACGTAACGGGGCGAAAATTATCGTCTGCGATCCGCGC 1370      1380      1390      1400      1410      1420      1430      1440
AAAATTGAAACCGCGCGCATTGCTGACATGCACATTGCACTGAAAAACGGCTCGAACATCGCGCTGTTGAATGCGATGGG 1450      1460      1470      1480      1490      1500      1510      1520
CCATGTCATTATTGAAGAAAATCTGTACGACAAAGCGTTCGTCGCTTCACGTACAGAAGGCTTTGAAGAGTATCGTAAAA
```

FIG.1a

```
         1530      1540      1550      1560      1570      1580      1590      1600
TCGTTGAAGGCTACACGCCGGAGTCGGTTGAAGATATCACCGGCGTCAGCGCCAGTGAGATTCGTCAGGCGGCACGGATG
         1610      1620      1630      1640      1650      1660      1670      1680
TATGCCCAGGCGAAAAGCGCCGCCATCCTGTGGGGCATGGGTGTAACCCAGTTCTACCAGGGCGTGGAAACCGTGCGTTC
         1690      1700      1710      1720      1730      1740      1750      1760
TCTGACCAGCCTCGCGATGCTGACCGGTAACCTCGGTAAGCCGCATGCGGGTGTTAACCCGGTTCGTGGTCAGAACAACG
         1770      1780      1790      1800      1810      1820      1830      1840
TTCAGGGTGCCTGCGATATGGGCGCGCTGCCGGATACGTATCCGGGATACCAGTACGTGAAAGATCCGGCTAACCGCGAG
         1850      1860      1870      1880      1890      1900      1910      1920
AAATTCGCCAAAGCCTGGGGCGTGGAAAGCCTGCCAGCGCATACCGGCTATCGCATCAGCGAGCTGCCGCACCGCGCAGC
         1930      1940      1950      1960      1970      1980      1990      2000
GCATGGCGAAGTGCGTGCCGCGTACATTATGGGCGAAGATCCGCTACAAACTGACGCGGAGCTGTCGGCAGTACGTAAAG
         2010      2020      2030      2040      2050      2060      2070      2080
CCTTTGAAGATCTGGAACTGGTTATCGTTCAGGACATCTTTATGACCAAAACCGCGTCGGCGGCGGATGTTATTTTACCG
         2090      2100      2110      2120      2130      2140      2150      2160
TCAACGTCGTGGGGCGAGCATGAAGGCGTGTTTACTGCGGCTGACCGTGGCTTCCAGCGTTTCTTCAAGGCGGTTGAACC
         2170      2180      2190      2200      2210      2220      2230      2240
GAAATGGGATCTGAAAACGGACTGGCAAATCATCAGTGAAATCGCCACCCGTATGGGTTATCCGATGCACTACAACAACA
         2250      2260      2270      2280      2290      2300      2310      2320
CCCAGGAGATCTGGGATGAGTTGCGTCATCTGTGCCCGGATTTCTACGGTGCGACTTACGAGAAAATGGGCGAACTGGGC
         2330      2340      2350      2360      2370      2380      2390      2400
TTCATTCAGTGGCCTTGCCGCGATACTTCAGATGCCGATCAGGGGACTTCTTATCTGTTTAAAGAGAAGTTTGATACCCC
         2410      2420      2430      2440      2450      2460      2470      2480
GAACGGTCTGGCGCAGTTCTTCACCTGCGACTGGGTAGCGCCAATCGACAAACTCACCGACGAGTACCCGATGGTACTGT
         2490      2500      2510      2520      2530      2540      2550      2560
CAACGGTGCGTGAAGTTGGTCACTACTCTTGCCGTTCGATGACCGGTAACTGTGCGGCACTGGCGGCGCTGGCTGATGAA
         2570      2580      2590      2600      2610      2620      2630      2640
CCTGGCTACGCACAAATCAATACCGAAGACGCCAAACGTCTGGGTATTGAAGATGAGGCATTGGTTTGGGTGCACTCGCG
         2650      2660      2670      2680      2690      2700      2710      2720
TAAAGGCAAAATTATCACCCGTGCGCAGGTCAGCGATCGTCCGAACAAAGGGGCGATTTACATGACCTACCAGTGGTGGA
         2730      2740      2750      2760      2770      2780      2790      2800
TTGGTGCCTGTAACGAGCTGGTTACCGAAAACTTAAGCCCGATTACGAAAACGCCGGAGTACAAATACTGCGCCGTTCGC
         2810      2820      2830      2840      2850      2860      2870      2880
GTCGAGCCGATCGCCGATCAGCGCGCCGCCGAGCAGTACGTGATTGACGAGTACAACAAGTTGAAAACTCGCCTGCGCGA
         2890      2900      2910      2920      2930      2940      2950      2960
AGCGGCACTGGCGTAATACCGTCCTTTCTACAGCCTCCTTTCGGAGGCTGTTTTTTTATCCATTCGAACTCTTTATACTG
         2970      2980      2990      3000      3010      3020      3030      3040
GTTACTTCCCG
```

β-galactosidase activity after expression of the plasmids pBN208, pBN210 and pBN211.

DNA FOR THE REPRESSIBLE AND INDUCIBLE EXPRESSION OF FOREIGN GENES

The present invention is concerned with recombinant DNA and expression vectors, with processes for the production of such recombinant DNA and expression vectors, as well as with the use thereof for the inducable and repressible expression of a foreign gene.

An important object of the applied gene technology is the production of protein from recombinant DNA. For this purpose, a special class of vectors, the so-called expression vectors, is needed. These possess not only the structural prerequisites for the cloning, transfer and multiplication of recombinant DNA but also for the expression of a protein. For this purpose, these recombinant DNA molecules require special regulation sequences, so-called promotors, which bring about the transcription of the DNA sequence in RNA, the translation of which by the ribosomes leads to the final protein.

DNA regions to which RNA polymerase must bind for the transcription of one or more genes are called promotors. Many such promotors have common structural features, the importance of which is believed to lie, inter alia, in their interaction with certain proteins. However, by such interactions with cellular proteins or other molecules, there can also be brought about an induction of the activity of the promotor. One example of this is the interaction of the lambda promoter $P_1$ with the lambda repressor cI.

In the case of the gene-technological production of proteins, it is of special advantage when a promotor present in the expression vector can be regulated by the presence of or by the addition of repressors or inducers. Hitherto, however, it has only been possible to bring about such a repression or induction by the addition of an inducer or by the use of temperature-sensitive micro-organisms with a precisely maintained temperature change. Most of the inducers used are very expensive and the processes employed for the induction or repression are complicated and only of limited suitability for the regulation of the expression of a protein.

Therefore, it is an object of the present invention to provide recombinant DNA and expression vectors which, in the simplest possible way, make possible regulation of the expression of a desired gene product, as well as increased rates of expression of the gene product.

Thus, according to the present invention, there is provided recombinant DNA, wherein it contains the consensus sequence.

```
    T    TTTC    T          A   A   T
AT  TCG       G  CACGTC  A    AC   G
G        AAAT A          G  C    G
``` and a promotor which has the DNA sequence $GGN_{10}GC$.

Due to the presence of this DNA consensus sequence, one achieves a promoter downstream of that sequence which has the DNA sequence $GGN_{10}GC$, is repressed by oxygen, wheras it is induced by formate under anaerobic conditions.

The DNA consensus sequence is preferably present 15 to 150 base pairs upstream (i.e. on the 5'-side) from the transcription start of a gene expressed under the control of the promotor, the promotor being present between the consensus sequence and the transcription start. In an especially preferred embodiment, the consensus sequence lies 80 to 130 base pairs upstream of the transcription start.

As promotors, there can be used the fdhF promotor, a promotor of a transcription unit essential for the expression of hydrogenase or essential structural elements of the ntrA-dependent promotors, insofar as they contain the above-mentioned DNA sequence. The fdhF promotor is preferably used.

The present invention also provides an expression vector which contains the recombinant DNA according to the present invention ligated into an appropriate vector. As vectors, there can be used the vectors normally employed, for example pBR322 or pUC vectors. In addition, an expression vector according to the present invention can contain a polylinker downstream of the promotor which simplifies the introduction of any desired foreign gene by the presence of several restriction cleavage sites.

In addition, the present invention provides the plasmid pBN80, DSM 4073P, which contains 240 base pairs of the 5' flanking region of the fdhF gene (+1 means the translation start). In this upstream region of the fdhF gene, there is contained not only the above-mentioned DNA consensus sequence but also the fdhF promotor which has the DNA sequence GGN GC. This plasmid displays an inducible tetracycline resistance, which is repressible by oxygen and inducible by formate under anaerobic conditions. Furthermore, however, it is also possible, by cleavage with appropriate restriction nucleases and ligation, to insert a further foreign gene into this plasmid and to control the expression thereof in the above-mentioned way.

Furthermore, the present invention provides a process for the production of the recombinant DNA according to the present invention, wherein a DNA sequence containing the consensus sequence is identified from a gene bank of a micro-organism, which contains a gene which is repressible by oxygen and inducible by formate under anaerobic conditions, isolated and combined with an appropriate promotor containing DNA sequence $GGN_{10}GC$ according to known methods.

For the identification of this DNA sequence, there can be carried out, for example, a hybridization or coupling to an indicator gene and testing of the expression under aerobic and anaerobic conditions.

The DNA sequence is preferably isolated from *Escherichia coli*, DSM 2093, DSM 2102, or from *Salmonella typhimurium*, DSM 554. Analogously to this process for the isolation of a DNA fragment, instead of a DNA fragment which only contains the consensus sequence, the whole upstream region of a gene inducible by formate and repressible by oxygen which contains not only the consensus sequence but also a promotor which, in turn, contains the DNA sequence $GGN_{10}GC$ can be isolated. This preferably takes place by isolating the upstream region of the fdhF gene or of a transcription unit essential for hydrogenase expression.

The present invention also provides a process for the production of an expression vector which contains the recombinant DNA. In this process, the recombinant DNA sequence which has been isolated and either contains the consensus sequence connected to an appropriate promoter or contains the upstream region of a gene which contains both the consensus sequence and a promotor and which is inducible by formate and repressible by oxygen, is inserted into an appropriate vector. Optionally, the recombinant DNA sequence also contains a promotor. As vectors, there can hereby be used the above-mentioned vectors but also all other vectors appropriate for the expression of foreign genes.

The process according to the present invention for the production of the plasmid pBN80, DSM 4073P, is characterised in that the upstrear: region of the fdhF gene from −240 bp before the translation start is inserted into the vector pGA46, DSM 4068P which has been, cleaved with PstI and 8glII.

The use according to the present invention of a recombinant DNA or of an expression vector, as are described hereinbefore, for the inducible and repressible expression of a foreign gene is characterized in that the induction is brought about under anaerobic conditions by formate and the repression by oxygen.

The expression can hereby be carried out in an appropriate microorganism from the family Enterobacteriaceae, preferably in *Escherichia coli* or *Salmonella typhimurium*.

The expression is preferably carried out in a host strain which is ntrA positive.

The ntrA gene product plays an important role in the anaerobic metabolism of micro-organisms. The ntrA gene product is, a sigma factor which changes the promotor selectivity of the RNA polymerase enzyme in such a manner that it recognizes the promotor sequences contained in the recombinant DNA and expression vectors of the present invention. The use according to the present invention of the recombinant DNA or expression vectors of the present invention is admittedly also possible without the presence of the ntrA gene product but the ntrA gene product strengthens the expression of the foreign gene quite substantially.

If a host strain is used which is ntrA-, there are, nevertheless, two possibilities for introducing the ntrA gene product into the cell. One possibility is to ligate the ntrA gene into the recombinant DNA or the expression vector which also carries the desired gene simultaneously the expression of the ntrA gene product or, however, to introduce the ntrA gene cloned in an additional vector into the host cells. The production of the ntrA gene is then independent of that of the foreign gene but this is, nevertheless, positively influenced by the ntrA gene product.

For the introduction into a host cell via either the recombinant DNA or the expression vector or on an additional vector, an ntrA gene corresponding to the host cell is preferred. In this way, expression of the foreign gene gives significantly better results than when a foreign ntrA gene is used, as will be seen in the last line of the Table which follows.

By means of recombinant DNA and expression vectors according to the present invention, it is possible, in a simple way, to regulate the expression of a foreign gene. Thus, for example, in the aerobic early growth phase of the micro-organism used, a possibly disturbing expression of the foreign gene is suppressed. In the case of transition into the late logarithmic, anaerobic growth phase, the expression is then induced by formate formed by the micro-organism and strengthening of the expression is achieved by the addition of formate to the growth medium of the micro-organism. In this way, introduction of inducer in order to stimulate cells in different stages of the growth phase to express the foreign gene, can be avoided. This is desirable because the inducer can possibly hinder further growth and could have a negative effect on the cell itself. In the anaerobic late logarithmic growth phase, the cells have already matured and have achieved optimum density. An oxygen limitation there takes place automatically and can be further reinforced or regulated by fermentation techniques. Due to the high cell density of the micro-organisms, an optimum expression of the foreign gene can be achieved.

Therefore, the use of the expression vectors according to the present invention for the production of proteins of great interest is an economic and simpple possibility for the regulation since an expensive and complicated induction (like inducer addition and temperature shift) is no longer necessary.

BRIEF DESCRIPTION OF THE DRAWINGS

FIG. 1 shows the nucleotide sequence of the fdhF gene, including the 5'-upstream region;

Figure 2:
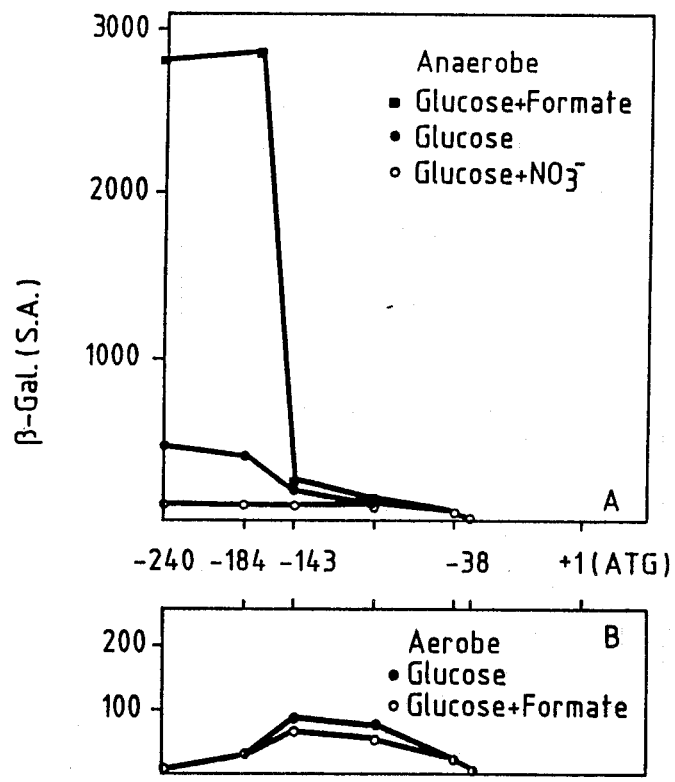
FIG. 2 shows the β-galactosidase activity after expression of the plasmids pBN 208, pBN 210 and pBN 211 under anaerobic (A) and under aerobic (B) growth conditions.

The following Examples are given for purposes of illustrating the invention.

EXAMPLE 1

Construction of fdhF-lacZ fusion plasmids

The AatII fragment (approximately 1.5 kb) of the plasmid pBN2, DSM 4072P, an fdhF-lacZ fusion plasmid (Proc. Natl. Acad. Sci. U.S.A., 83, 4650–4654/1986) was isolated by preparative agarose gel electrophoresis and incubated at 20° C. for different periods of time with 0.2 U/μg DNA Bal31 exonuclease. After filling in the overhanging 5' ends with DNA polymerase (Klenow fragment), the fragments were ligated with EcoRI linkers (dGGAATTCC) and subsequently digested with restriction endonucleases EcoRI and BamHI. The fragment mixture was separated by preparative agarose gel electrophoresis and three large fractions (compared with restriction fragments of known size as length markers) were eluted from the gel. These fragments were cloned into the multilinker site of the plasmid pMC1403, DSM 4067P. As recipient, *Escherichia coli* FM 911, DSM 4066P (MC 4100, fdhF, rec A56, lac−) was used. From this clones which were shortened from the 5'-end of the upstream region were obtained. In a second step, the shortest clone, pBN208, DSM 4069P, was isolated, linearized by digestion with EcoRI and incubated with 0.1 U/μg DNA Bal31 at 20° C. After filling in the overhanging 5'-ends, EcoRI linkers were again ligated and subsequently the DNA was cleaved with EcoRI and ClaI. There was obtained a series of fragments which were recloned into the EcoRI/ClaI digested vector pMC 1403, DSM 4067P. The plasmids obtained were again transformed into the *Escherichia coli* strain FM 911. The two clones pBN210, DSM 4070P, and pBN211, DSM 4071P, were isolated.

The transformation of the plasmids pBN2, pBN208, pBN210, pBN211 and pMC1403 into the strain FM911 (MC4100, fdhF, rec A56) was carried out substantially according to the method of Cohen et al. (see Cohen et al., PNAS, 69, 2110–2114/1977):

Early logarithmic cells were harvested after cooling to 0° C. and subsequently subjected to a treatment with ice-cold 50 mM aqueous calcium chloride solution. The addition of the DNA took place at 0° C. and, after an incubation for 45 minutes at 0° C., a heat shock was carried out at 43° C. for 4 minutes. After cooling to ambient temperature, the cells were incubated in rich medium at 37° C. for 1 hour for phenotypic expression. The selection for ampicillin resistance in the case of the plasmids pBN2, pBN208, pBN210, pBN211 and pMC1403 took place on plates with 100 µg./ml. ampicillin.

The precise deletion end points, that is the positions of the EcoRI linker, were determined by DNA sequencing according to the method of Maxam and Gilbert (see Methods of Enzymology, 65, 499-560/1980.

In FIG. 1 of the accompanying drawings the nucleotide sequence of the fdhF gene is shown, including the 5'-upstream region, ATG indicating the start of the translation. From the Figure the remaining fdhF promotor region of the plasmids pBN208, pBN210 and pBN211 can be seen.

EXAMPLE 2

Comparison of β-galactosidase expression of the plasmids pBN208, pBN210 and pBN211.

The fdhF-lacZ fusion plasmids obtained in the manner described in Example 1 were investigated under anaerobic and aerobic growth conditions for expression of β-galactosidase activity. β-galactosidase activity was determined according to the method of J. H. Miller (see Experiments in Molecular genetics, Cold Spring Harbor Laboratory, Cold Spring Harbor, N.Y., 1972) and the specific activity was calculated. The result is shown in FIG. 2 of the accompanying drawings. FIG. 2A gives the results of the expression under anaerobic conditions and FIG. 2B under aerobic growth conditions. On the abscissa the end point of the deletion is given. This means the position of the EcoRI linker upstream of the translation start (position +1). The EcoRI linker at −240 corresponds to plasmid pBN208, at −184 to plasmid pBN210 and at −143 to plasmid pBN211. Nitrate was added to an end concentration of 10 mM and formate to an end concentration of 30 mM.

EXAMPLE 3

Production of plasmid pBN80, DSM 4073P

The 1.11 Kb BamHI/PstI fragment of the plasmid pBN208 was isolated by preparative gel electrophoresis and subsequently cloned into the vector pGA46, DSM 4068P, which had been cleaved with the restriction endonucleases PstI and BglII. In the recombinant plasmids the β-lactamase gene was reconstituted. The ligated plasmid pBN80, DSM 4073P, was then transformed into Escherichia coli FM911, as described in Example 1 for the plasmids pBN2, pBN208, pBN210, pBN211 and pMC1403. After transformation it was selected against chloramphenicol resistance (30 µg./ml.) and ampicillin resistance 100 µg./ml.). The clones obtained were checked for their tetracycline resistance under aerobic and anaerobic conditions. On plates with phosphate-buffered (pH 7) rich medium (with 0.8% glucose), the clones were tetracycline-sensitive under aerobic conditions. Under anaerobic conditions, tetracycline resistance was expressed and induced with formate (30 mM). Under anaerobic conditions in the presence of 50 mM nitrate, the clones were, on the other hand, tetracycline-sensitive.

EXAMPLE 4

Effect of an ntrA mutation on the expression of the fdhF-lacZ fusion gene

For the investigation of the effects of the mutation in ntrA gene, the β-galactosidase activity was investigated under aerobic and anaerobic conditions in two different strains of Escherichia coli, both of which had been transformed with the plasmid pBN208, DSM 4069P, which contained the fdhF-lacZ fusion gene. For this purpose, Escherichia coli strain FM909, DSM 4279, which is ntrA positive, as well as Escherichia coli strain BN950, DSM 4278, which is ntrA negative were used. The Escherichia coli strains were cultured in TGYEP medium (pH 6.5) (see Begg et al., FEMS Mikrobiol. Let., 2, 47-50/1977) containing 0.2% w/v of glutamine and the given amounts of formate or nitrate. In addition, the strain BN950, DSM 4278, was transformed with three further plasmids, namely, pBN17, DSM 4280P, pBN18 (see Example 6) and pBN61, DSM 4281P. The two plasmids pBN17 and pBN18 contained the ntrA gene from Klebsiella pneumoniae in different orientation ligated into a vector. The plasmid pBN61 contains the ntrA gene of Escherichia coli ligated into a vector. It is isolated by introducing a 2.7 kb-sized fragment from Escherichia coli DNA into the BamHI cleavage site of the vector pACYC184 (J. Bacteriol., 134, 1141-1156/1978). For these transformed strains, too, the expression of the β-galactosidase in the given growth medium of the Escherichia coli strains was investigated. The results are given in the following Table.

EXAMPLE 5

Construction of pBN17

The 1.96 kb ClaI fragment of the plasmid pMM17 (sequence: Nucl. Acids Res., 13, 7607-7620/1985) was cloned into the vector pACYC184 (J. Bacteriol., 134, 1141-1156/1978) in the ClaI cleavage site. The vector pBN17 (DSM 4280P) was obtained which contained the ntrA gene and was cleaved by treatment with EcoRV into fragments with lengths of 1.35 kb/750b and 3.83 kb.

EXAMPLE 6

Construction of pBN18 pBN18 contains the ntrA gene in the reverse orientation from pBN17 and was produced by cleavage of pBN17 with ClaI and subsequent ligation with T4-ligase. The plasmid pBN18 can be characterized as follows: after digestion with the restriction endonuclease EcoRV fragments of 1.35 kb/150b and 4.43 kb are obtained.

TABLE

| | | β-galactosidase activity (units) | | | | |
|---|---|---|---|---|---|---|
| strain | genotype | glucose (anaerobic) | glucose plus 30 mM formate (anaerobic) | glucose plus 10 mM nitrate (anaerobic) | glucose (anaerobic) | glucose plus 30 mM formate (anaerobic) |
| FM909 (pBN208) | ntra+ (fdhF::lacZ) | 340 | 1310 | 115 | 60 | 72 |
| BN950 (pBN208) | ntrA− (fdhF::lacZ) | 235 | 380 | 130 | 52 | 60 |

TABLE-continued

| strain | genotype | glucose (anaerobic) | glucose plus 30 mM formate (anaerobic) | glucose plus 10 mM nitrate (anaerobic) | glucose (anaerobic) | glucose plus 30 mM formate (anaerobic) |
| --- | --- | --- | --- | --- | --- | --- |
| | | | β-galactosidase activity (units) | | | |
| BN950 (pBN208, pBN17) | ntrA$^-$ (fdhF::lacZ, °ntrA$_k$$^+$) | 125 | 710 | 30 | n.d.* | n.d. |
| BN950 (pBN208, pBN18) | ntrA$^-$ (fdhF::lacZ, °ntrA$_k$$^+$) | 220 | 1075 | 85 | n.d. | n.d. |
| BN950 (pBN208, pBN61) | ntra$^-$ (fdhF::lacZ, °ntrA$_e$$^+$) | 1083 | 3016 | 147 | n.d. | n.d. |

*n.d. not determined
°The index k means that this gene originated from *Klebsiella pneumoniae* and the index e means that this gene orginated from *Escherichia coli.*

The following were deposited at the Deutsche Sammlung von Mikroorganismen, Mascheroder Weg 1b, D-3300, Braunschwerg, FRG:

| Name | Deposit ID |
| --- | --- |
| plasmid pBN 80 | DSM 4073P |
| E. coli DSM 2093 | DSM 2093 |
| E. coli DSM 2102 | DSM 2102 |
| S. typhimurium DSM 554 | DSM 554 |
| vector pGA 46 | DSM 4068P |
| pBN 2 | DSM 4072P |
| pMB 1403 | DSM 4067P |
| E. coli FM 911 | DSM 4066P |
| pBN 208 | DSM 4069P |
| pBN 210 | DSM 4070P |
| pBN 211 | DSM 4071P |
| E. coli FM 909 | DSM 4279 |
| E. coli BN 950 | DSM 4278 |
| pBM 17 | DSM 4280P |
| pBN 61 | DSM 4281P |

We claim:

1. Recombinant DNA comprising consensus sequence

```
      T    TTTC   T           A    A    T
   AT TCG        G  CACGTC   A   AC   G
      G    AAAT  A           G   C    G
``` and a promotor which contains the DNA sequence GGN$_{10}$GC.

2. Recombinant DNA according to claim 1, further comprising a gene whose expression is controlled by said promotor, wherein said consensus sequence is present from 15 to 150 base pairs upstream from the transcription start of said gene and said promotor is present between said consensus sequence and said transcription start point.

3. Recombinant DNA according to claim 2, wherein the consensus sequence is present 80 to 130 bp upstream of the transcription start point.

4. Recombinant DNA according to claim 1, wherein said promotor is a promotor of a transcription unit essential for hydrogenase expression.

5. Recombinant DNA according to claim 1, wherein said promotor contains essential structural elements of at least one ntrA-dependent promotor.

6. Recombinant DNA of claim I, wherein said promotor is the fdhF promotor.

7. An expression vector comprising recombinant DNA containing consensus sequence

```
      T    TTTC   T           A    A    T
   AT TCG        G  CACGTC   A   AC   G
      G    AAAT  A           G   C    G
``` and a promotor which contains DNA sequence GGN$_{10}$GC, said recombinant DNA ligated into a carrier vector.

8. Expression vector according to claim 7, further comprising a polylinker for the introduction of a foreign gene.

9. Process for the production of recombinant DNA containing consensus sequence

```
      T    TTTC   T           A    A    T
   AT TCG        G  CACGTC   A   AC   G
      G    AAAT  A           G   C    G
``` and a promotor which contains DNA sequence GGN$_{10}$GC comprising identifying a DNA sequence containing said consensus sequence in a gene bank of a micro-organism containing a gene which is repressible by oxygen and inductible by formate under anaerobic conditions, isolating said DNA sequence and combining said DNA sequence with a promotor containing said promotor DNA sequence to obtain said recombinant DNA.

10. Process according to claim 9, wherein the DNA sequence is isolated from the gene bank of a microorganism of the Enterobacteriaceae group.

11. Process according to claim 10, wherein the DNA sequence is isolated from *Escherichia coli,* DSM 2093 or 2102, or from *Salmonella typhimurium,* DSM 554.

12. Process according to claim 9 comprising isolating a whole upstream region of a gene inductible by formate and repressible by oxygen said gene containing said consensus sequence and a promotor containing said promotor sequence.

13. Process according to claim 12, wherein said gene is the fdhF gene.

14. Process according to claim 13 comprising ligating the upstream region of the fdhF gene from −240 bp down to the translation start point into vector pGA46, DSM 4068P following cleavage thereof with FstI and BglII to form plasmid pBN80, DSM 4073P.

15. Process according to claim 12, comprising isolating the upstream region of a promotor of a transcription unit essential for hydrogenase expression.

16. Process according to claim 9, further comprising inserting said recombinant DNA into a vector.

17. Process of claim 16, further comprising inserting a polylinker into said vector.

18. Recombinant plasmid pBN80, DSM 4073P.

19. Method for inducible or repressible expression of a foreign gene in a host cell, comprising treating a recombinant DNA sequence comprising a foreign gene, consensus sequence

```
    T    TTTC  T         A   A   T
AT  TCG        G  CACGTC A   AC  G
G       AAAT   A         G   C   G
``` and a promotor containing DNA sequence $GGN_{10}GC$ with formate under anaerobic conditions for inducing the expression and oxygen for repressing expression.

20. Method of claim 19 comprising expressing said recombinant DNA sequence in *Escherichia coli* or *Salmonella typhimurium*.

21. Method of claim 19 comprising expressing said recombinant DNA sequence is an ntrA-positive host cell.

22. Method of claim 19, wherein said recombinant DNA sequence further comprises a ntrA gene and said host cell is ntrA$^-$.

23. Method of claim 22, further comprising introducing an ntrA gene to an ntrA$^-$ host in a vector separate from said recombinant DNA.

24. Method of claim 23, wherein said ntrA gene is an ntrA gene native to said host cell.

25. Method of claim 22 wherein said ntrA gene is an ntrA gene native to said host cell.

* * * * *

UNITED STATES PATENT AND TRADEMARK OFFICE
CERTIFICATE OF CORRECTION

PATENT NO. : 4,963,482

DATED : October 16, 1990

INVENTOR(S) : Angelika Birkmann et al.

It is certified that error appears in the above-identified patent and that said Letters Patent is hereby corrected as shown below:

Column 2, line 26: "GGN GC" to -- $GGN_{10}GC$ --.

Column 3, line 10: "8glII" to -- BglII --.

Claim 23: change "22" to -- 19 --.

Signed and Sealed this

Twenty-fifth Day of August, 1992

*Attest:*

DOUGLAS B. COMER

*Attesting Officer*  Acting Commissioner of Patents and Trademarks